United States Patent
Abraham et al.

(10) Patent No.: US 6,812,249 B2
(45) Date of Patent: Nov. 2, 2004

(54) PROCESS FOR PREPARING A 3-HYDROXY-3-METHYLBUTYRATE AMINO ACID SALT AND METHOD OF USE

(76) Inventors: Sal Abraham, 1304 Electric St. East China Normal University, Chemical Dept., Dunmore, PA (US) 18509; Jie Tang, 3663 Zhong Shan Road (N) East China Normal University, Chemical Dept., Shanghai N/A 200062 (CN); Fan Yang, 3663 Zhong Shan Road (N), East China Normal University, Chemical Dept., Shanghai N/A, 200062 (CN); Shengli Jiang, 3663 Zhong Shan Road (N) East China Normal University, Chemical Dept., Shanghai N/A, 200062 (CN)

( * ) Notice: Subject to any disclaimer, the term of this patent is extended or adjusted under 35 U.S.C. 154(b) by 0 days.

(21) Appl. No.: 10/248,936

(22) Filed: Mar. 4, 2003

(65) Prior Publication Data

US 2004/0176449 A1 Sep. 9, 2004

(51) Int. Cl.[7] ............................................. A61K 31/19
(52) U.S. Cl. ...................... 514/557; 514/561; 514/565
(58) Field of Search ................................ 514/557, 561, 514/565; 562/579

(56) References Cited

U.S. PATENT DOCUMENTS

| | | |
|---|---|---|
| 4,992,470 A | 2/1991 | Nissen |
| 5,028,440 A | 7/1991 | Nissen |
| 5,348,979 A | 9/1994 | Nissen et al. |
| 5,360,613 A | 11/1994 | Nissen |
| 5,756,469 A | 5/1998 | Beale |
| 6,031,000 A | 2/2000 | Nissen et al. |
| 6,392,092 B2 | 5/2002 | McCoy et al. |

FOREIGN PATENT DOCUMENTS

WO    WO 99/66917    * 12/1999

OTHER PUBLICATIONS

Slater, G. et al. Int J Sport Nutr Exerc Metab. Sep. 2001;11(3):384–96, Human Kinetics Publishers, Inc., United States.

Slater, G. et al. Sports Med. Aug. 2000;30(2):105–16. Adis International Ltd., New Zealand.

Hu, Z. et al. The intestinal uptake of "Enzymatically–stable" peptide drugs in rats as influenced by D–Glucose in Situ. Life Sci. 1994;54(25):1977–85. Elsevier, United States.

Minami, G et al. Characteristics and mechanism of glutamine–dipeptide absorption in human intestine. Gastroenterology. Jul. 1992;103(1):3–11. Elsevier, United States.

* cited by examiner

*Primary Examiner*—Paul J. Killos

(57) ABSTRACT

This invention relates to a process for synthesis and method of use of an effective amount of a 3-hydroxy-3-methylbutyrate (HMB) amino acid salt for the regulation athletic function in humans.

12 Claims, No Drawings

PROCESS FOR PREPARING A 3-HYDROXY-3-METHYLBUTYRATE AMINO ACID SALT AND METHOD OF USE

BACKGROUND OF INVENTION

This invention relates to a process for the synthesis and method of use of an effective amount of a 3-hydroxy-3-methylbutyrate (HMB) amino acid salt for the regulation athletic function in humans. HMB synthesis traditionally has utilized many forms ranging from free acid, salt, ester, and lactone. HMB mineral salts have been the preferred form, which may consist of a sodium salt, a potassium salt, a magnesium salt, a chromium salt, and most preferably a calcium salt. This is most likely due to the fact that the mineral salts are thought to produce the most water soluble forms thereby possessing the most orally bioavailable forms. Although we purpose for the first time that the process for the synthesis and use of a HMB amino acid salt is novel, unobvious, and superior due to enhanced absorption, bioavailability and function.

HMB is a product of leucine metabolism. Leucine metabolism begins with the transanimation to the keto acid alpha-ketoisocaporate (KIC) which is then oxidized to HMB by KIC-dioxygenase. KIC continues to form ketones while HMB is utilized as a precursor to cholesterol. HMB enters the cytosol of liver and muscle and is converted to beta-hydroxy-beta-methylglutarate-Co-A (HMG-CoA), which is a precursor to cholesterol metabolism.

HMB has been patented for number of useful applications. For instance, U.S. Pat. No. 4,992,470 by Nissen demonstrates a method for enhancing immune response in mammals. U.S. Pat. No. 5,028,440 by Nissen describes a method for increasing lean tissue in animals. U.S. Pat. No. 5,348,979 by Nissen demonstrates a method for promoting nitrogen retention in humans. U.S. Pat. No. 5,360,613 by Nissen further demonstrates a method for reducing blood levels of total cholesterol and low-density lipoprotein cholesterol. More recently U.S. Pat. No. 6,392,092 by Mycoy et al. describes a process for the manufacturing of HMB salts in commercially viable amounts.

HMB mineral salts have been successfully utilized in a number of applications but it's uses with experienced weight trained athletes have not been as successful. Int J Sport Nutr Exerc Metab 2001 September; 11(3): 384–96 by Slater et al. and Sports Med 2000 Aug. 30(2): 105–16 by Kreider et al. demonstrates that experienced weight trained athletes do not respond in the same manner to supplemental HMB calcium salts as untrained individuals. Both researchers concluded that there was no alteration in muscle size, fat mass, or strength variables after either 6 weeks or 28 days of oral supplemental HMB calcium salt.

U.S. Pat. No. 5,756,469 by Beale describes a method for the use of pyruvate and/or pyruvyl amino acids in combination with anti-cortisol compounds (HMB) for increasing protein concentration In mammals. Beale states that this combination would have a beneficial impact on the treatment of catabolic conditions associated with diseases such as AIDS and cancer. Beale discloses that this combination was shown to produce a 15 percent increase of lean body mass in healthy rats. This invention represents an improvement in standard nutraceutical preparations due to the combination of pyruvate and/or pyruvyl amino acids and HMB. However this combination would not be efficacious In experienced weight trained athletes due to the economic impracticality of pyruvyl amino acids and the inferior function and bioavailability of orally combining ingredients versus covalently bonded compounds such as HMB amino acid salts.

U.S. Pat. No. 6,031,000 by Nissen describes a method for the use of combining HMB and at least one amino acid. The HMB utilized in this application consists of a sodium salt, a potassium salt, a magnesium salt, a chromium salt, and most preferably a calcium salt, which is the same as previous applications. The amino acids consist of L-isomer essential amino acids and/or a combination of L-glutamine and L-arginine. Nissen states that unlike traditional HMB supplementation resulting in increased muscle mass and deceased fat mass, the combination of HMB and at least one amino acid causes increased muscle mass without decreasing fat mass. This alteration in HMB functionality can be advantageous in animals suffering from body tissue wasting as the result of disease such as AIDS, although this application would not be desirable to most athletes due to the retention of fat mass. The efficacy of such a application with experienced weight trained athletes is not likely due to the well known fact to those skilled in the art that wasting conditions prime the body for weight gain whereas experienced weight trained athletes require potent stimuli in order to produce gains in muscle mass.

U.S. Pat. No. 6,392,092 by Mycoy et al. describes a process for the manufacturing of HMB salts in commercially viable amounts. Mycoy et al. states that HMB is only available in small quantities due to the absence of an efficient synthetic process for large commercial production. The chemical process of this invention utilizes diacetone alcohol to produce free or unbound HMB which is then combined with the appropriate salt. The disclosed chemical procedure is noted to produce a 70% increase in HMB output as compared to standard processes. This process represents an improvement in standard HMB salt production however it does not address production of novel HMB amino acid salts in small or large quantity.

SUMMARY OF INVENTION

The present invention consists of a process for the synthesis of a HMB amino acid salt and a method for the regulation of athletic function in humans. The method comprises administering to humans an effective amount of a composition consisting of an HMB amino acid salt such as but not limited to HMB-L-Arginine, HMB-L-Glutamine, HMB-Glycylarginine, HMB-Glycylglutamine. This novel combination creates an HMB amino acid salt in which both compounds are combined by a covalent bond.

The chemical synthesis of HMB amino acid salts consists of a three step process and is capable of producing small or very large commercial amount. The process begins with the preparation of an inorganic alkali solution, which is maintained at a temperature of about minus 25 degree Celsius to 50 degree Celsius. The next step involves the addition of an organic alcohol for the formation of a 3-hydroxy-3-methylbutyrate alcohol solution. The final step involves the addition of an amino acid to the solution, which is agitated for about 30 minutes to 3 hours under room temperature in order to produce the finished product consisting of a white crystalline powder. This entire process is novel and unobvious to those skilled in the art since the HMB acid is not separated from the reaction solution, the acid is directly extracted from the reaction solution. This HMB amino acid salt utilizes the peptide carrier system instead of hydrolysis in the gut thereby substantially increasing oral absorption and bioavailability of the intact compound. Once the intact compound enters the blood stream it exerts a dual effect since both HMB and the amino acid contribute to the accretion of lean tissue by different mechanisms. The present invention promotes the development of lean tissue but also decreases fat tissue unlike U.S. Pat. No. 6,031,000 by Nissen, which only promotes lean tissue by orally combining HMB and an amino acid. In fact the covalently bound HMB amino acid salt possess superior results to HMB alone or combined orally with various amino acids and therefore may be utilized as a method for the regulation of athletic function in experienced weight trained athletes.

DETAILED DESCRIPTION

The chemical term HMB amino acid salt, for instance HMB-L-Arginine refers to 3-hydroxy-3-methylbutyrate-L-arginine with a molecular weight of 292.33. Possible alternative amino acid salts of HMB include the use of all essential and non-essential L-form, D-form, and DL-form amino acids and dipeptides such as HMB-Glycylarginine, HMB-Clycylglutamine, HMB-Alanylarginine, and HMB-Alanylglutamine. This invention concerns a HMB amino acid salt in various ratios preferably a 1:1 ratio and all previously mentioned alternatives. The previous examples of various ratios and amino acid salts are presented by way of illustration only. It should be understood that this invention is not construed as limited in scope by the details contained therein, as it is apparent to those skilled in the art that modifications in materials and methods can be made without deviating from the scope of the invention.

The first step in the synthesis of a HMB amino acid salt consists of the preparation of an inorganic alkali. The inorganic alkali is dissolved in water under agitation. The solution is cooled to about 25 degree Celsius to 50 degree Celsius. A halogen is dropwise added to the solution, the temperature is maintained between 25 degree Celsius to 50 degree Celsius. The prepared acid solution is kept at around minus 25 degree Celsius to 50 degree Celsius.

The next step involves the preparation of 3-hydroxy-3-methylbutyrate (HMB). The previously prepared acid solution is dropwise added to a solution of organic alcohol in water, agitated for 1 to 10 hours. Then a inorganic anion is added to decolour the solution. Then an inorganic anion is added to decolor the solution.

The water layer is adjusted to a ph of about minus 4 to 7 with a dilute inorganic acid, and extracted by an organic alcohol.

The final step consists of the addition of the amino acid salt. The water is added to the above prepared alcohol solution. The amino acid is added to the solution and agitated for about 30 minutes to 3 hours under room temperature. The water layer is separated from the mixture, and the water is removed under vacuum to provide the HMB amino acid salt. Other amino acids and amino acid derivatives can be similarly prepared for the synthesis of HMB amino acid salts. This process has been designed for either efficient small or efficient large scale production by simply adjusting the amounts of the ingredients accordingly.

In vivo and vitro research by Minami et. al. Gastroenterology 1992 July;103(1):3–11 demonstrates that glutamine absorption is enhanced by dipeptide forms. The researchers utilized free glutamine, glycylglutamine and alanylglutamine. They noted the uptake of peptide-bound glutamine by brush border membrane vesicles was not inhibited by deletion of sodium or addition of free amino acids to the incubation medium but was inhibited by other oligopeptides and stimulated by a proton gradient. Minami et al. concluded that the predominant route of glutamine dipeptide absorption in the human intestine Is by intact peptide known as the peptide carrier system rather than hydrolysis.

The peptide carrier system is a unique method of intestinal delivery that benefits peptides up to 3 residues in length. In other words di- and tripeptides utilize the peptide carrier system and thus are absorbed intact by the intestine whereas tetrapeptides and greater are absorbed by hydrolysis and broken down in order for intestinal absorption to take place. HMB amino acid salts and amino acid mineral chelates utilize this system of enhanced delivery and thus possess superior function. Amino acid salts and chelates made with one, two, or three amino acids are absorbed without digestion in the intestines resulting in greater absorption and effectiveness. All previous forms of HMB are absorbed by hydrolysis limiting the amount of active HMB entering the plasma thus limiting effectiveness.

HMB amino acid salts may also be combined with D-glucose or any insulin potentiating agent as an excipient, coating, or free powder for enhanced absorption beyond the peptide carrier system. Research by Hu Z. et al. Life Sci 1994;54(25):1977–85 demonstrates that that glucose enhances jejunal permeabilities of smaller peptides by solvent drag and the enhancement is limited in situ by peptide molecular size. The studies with nonmetabolizable 3-O-methylglucose suggest that the augmentation of the proton gradient across the transmucosal membrane by glucose contributes to the carrier-mediated transport observed with the smaller peptides. Thus glucose or any insulin potentiating agent can be utilized to further enhance the bioavailability of compounds that are transported by the enhanced delivery of the peptide carrier system. The enhanced absorption and bioavailability lead to enhanced function due to the delivery of the HMS amino acid salt intact into plasma. HMB amino acid salts are superior to all previous forms of HMB due to enhanced absorption, bioavailability and function. It has been noted in the literature that all previous forms of HMB do not exhibit enhanced absorption or bioavailability from the peptide carrier system and/or from glucose.

The HMB amino acid salt promotes lean tissue and strength while decreasing fat tissue unlike U.S. Pat. No. 6,031,000 by Nissen, which only results in the promotion of lean tissue. Thus the said compound can be given to humans either in conjunction with or without a high protein diet (1.25 to 1.8 grams protein/kilogram of body weight) and proper anaerobic training program in order to increase the variables associated with athletic function for the purpose of enhancing physical performance. Therefore this compound represents an improvement in standard dietary HMB supplementation, which may now be utilized with experienced weight trained humans for the regulation of athletic performance due to superior function.

After an extensive review of the scientific literature regarding the novel and unobvious synthesis of HMB amino acid salts and their superior absorption, bioavailability, and function, it then became the focus of this invention that HMB amino acid salts could be administrated perorally as an effective means of regulating athletic function in experienced weight trained humans by promoting lean body mass and decreasing fat mass. The oral daily doses can be between 1 to 9,000 mg. per day. The preferred daily dosing schedule should be divided into 3 sub dose applications per day in order maintain adequate blood concentrations. In addition to peroral use, HMB amino acid salts can be effectively administered by several other routes and dosage forms including transdermal, sublingual, intranasal, capsules, tablets, caplets, liquid, powder and functional food products.

The following examples illustrate a process for synthesis and method of use of a HMB amino acid salt. The following examples should not be considered as limitations of the present invention.

EXAMPLE 1

Synthesis of HMB-L-Arginine Amino Acid Salt

The first step in the synthesis of HMB-L-Arginine consists of the preparation of sodium hypobromide. 100 portions of sodium hydroxide are dissolved in 400 portions of water under agitation. The solution is cooled to 0 Celsius. 192 portions of bromine are dropwise added to the solution, the temperature is maintained between 0 degree Celsius to 5 degree Celsius. The prepared sodium hypobromide solution is kept at 0 degree Celsius to 5 degree Celsius.

The previously prepared sodium hypobromide is dropwise added to a solution of 46 portions of diacetone alcohol in 120 portions of water, agitated for 6 hours. Then 8 portions of sodium bisulfite are added to decolour the solution. The organic layer is separated from the mixture. The water layer is adjusted to a pH of 2 to 3 using dilute hydrochloric acid, and extracted by isobutanol.

120 portions of water are added to the above prepared isobutanol solution. 28 portions of L-Arginine are added to the solution and agitated for 1 hour under room temperature. The water layer is separated from the mixture, and the water is removed under vacuum. 46.4 portions of HMB-L-arginine are obtained as white crystalline powder with melting point 116 to 130 Celsius.

EXAMPLE 2

HMB-L-arginine Amino Acid Salt Method of Use

In this example the experienced weight trained athlete orally consumes 1 gram of HMB-L-arginine divided 3 times throughout the day wherein the 1 gram of HMB-L-arginine is pressed into a tablet and coated with D-glucose. Once in the plasma HMB-L-arginine then exerts a synergistic lean tissue promoting effect due to the anti-catabolic actions of HMB and the nitric oxide releasing properties of L-arginine.

HMB promotes the accretion of lean tissue and loss of fat tissue via increased nitrogen retention. L-arginine promotes the release of nitric oxide for increased blood flow to the muscle resulting in greater glucose and amino acid uptake which in turn activates protein synthesis and promotes muscular strength. The previously mentioned increase in lean body mass and loss of fat tissue is predominately associated with the anti-catabolic and hemodialating effects of HMB-L-arginine. This increase in lean body mass and strength coupled with the loss of fat tissue contributes to the regulation of athletic function and thus leads to enhanced physical performance.

The foregoing descriptions of the invention are for illustration only. Modifications not included in the description, which are obvious to those skilled in the art, are intended to be included in the scope of the following claims.

What is claimed is:

1. A process for the synthesis of 3-hydroxy-3-methylbutyrate or an amino acid salt thereof, in a molar ratio of 0.1:100 to 100:0.1 comprising the steps of:
    a) reacting an inorganic alkali in water and combining a halogen at a temperature of minus 25 degrees to 50 degrees Celsius to provide an acid solution,
    b) reacting the product of step a) in an organic alcohol and water solution;
    decoloring the solution with an inorganic anion;
    adjusting the water layer to a ph of minus 4 to 7 with an inorganic acid;
    and extracting the water layer with an organic alcohol to provide a HMB alcohol solution,
    c) reacting the product of step b) in water and combining an amino acid at 1 to 100 degree Celsius;
    separating the water layer from the mixture; and
    removing the water under vacuum for the recovery of the 3-hydroxy-3-methylbutyrate amino acid salt.

2. The process according to claim 1, wherein the said molar ratio is 0.1:1 to 1:0.1.

3. The process according to claim 1 step a), wherein the reaction is carried out at a temperature of 0 degree Celsius to 5 degrees Celsius.

4. The process according to claim 1 step a), wherein said inorganic alkali is sodium hypobromide; said halogen is bromine; and said acid solution is sodium hypobromide.

5. The process according to claim 1 step b), wherein the reaction is carried out at a temperature of 2 degrees Celsius to 3 degrees Celsius.

6. The process according to claim 1 step b), wherein said organic alcohol is diacetone alcohol; said inorganic anion is sodium bisulfite; said inorganic acid is hydrochloric acid; and the water extracting organic alcohol is isobutanol.

7. The process according to claim 1 step c), wherein the reaction is carried out at a temperature under 22 degrees Celsius.

8. The process according to claim 1 step c), wherein said amino acid is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, pyrrolysine, serine, threonine, tryptophan, tyrosine, valine, and combinations thereof, and dipeptides and tripeptides formed by any combination of said amino acids thereof and L-form, D-form, and DL-form steroisomers of said amino acids thereof.

9. A method for providing 3-hydroxy-3-methylbutyrate to a human, comprising: receiving a 3-hydroxy-3-methylbutyrate amino acid salt by the human, wherein the 3-hydroxy-3-methylbutyrate amino acid salt is suitable for being modified by the human to form 3-hydroxy-3-methylbutyrate.

10. The method as described in claim 9, wherein the 3-hydroxy-3-methylbutyrate amino acid salt is suitable for peroral, transdermal, sublingual, and intranasal administration.

11. The method as described in claim 9, wherein the 3-hydroxy-3-methylbutyrate amino acid salt is suitable in a daily dose of 1 to 9,000 mg/day.

12. The method as described in claim 9, wherein the 3-hydroxy-3-methylbutyrate amino acid salt is received by the human, the 3-hydroxy-3-methylbutyrate amino acid salt is modified by the human into 3-hydroxy-3-methylbutyrate and an amino acid.

* * * * *